(12) United States Patent
Sommer et al.

(10) Patent No.: US 7,182,107 B2
(45) Date of Patent: Feb. 27, 2007

(54) BIOLOGICAL ADHESIVE LOADING STATION AND METHOD

(75) Inventors: Eric Sommer, Rancho Cordova, CA (US); Philip Henry Coelho, Rancho Cordova, CA (US); Phil Kingsley, Mather, CA (US)

(73) Assignee: ThermoGenesis Corp., Rancho Cordova, CA (US)

( * ) Notice: Subject to any disclaimer, the term of this patent is extended or adjusted under 35 U.S.C. 154(b) by 317 days.

(21) Appl. No.: 10/737,066

(22) Filed: Dec. 15, 2003

(65) Prior Publication Data

US 2004/0140012 A1   Jul. 22, 2004

(51) Int. Cl.
   *B65B 1/04* (2006.01)
(52) U.S. Cl. .............. 141/9; 141/99; 141/100; 141/104; 141/114; 141/236
(58) Field of Classification Search .............. 141/9, 141/99, 100, 104, 114, 236
   See application file for complete search history.

(56) References Cited

U.S. PATENT DOCUMENTS

| | | | |
|---|---|---|---|
| 1,948,388 A | 2/1934 | Liberson | |
| 3,949,746 A | 4/1976 | Wallach | |
| 4,166,533 A | 9/1979 | Maitland | |
| 4,454,773 A * | 6/1984 | Brunner et al. | 141/236 |
| 4,666,429 A | 5/1987 | Stone | |
| 4,795,441 A | 1/1989 | Bhatt | |
| 4,954,239 A | 9/1990 | Mueller | |
| 5,014,715 A * | 5/1991 | Chapolini | 600/485 |
| 5,037,390 A | 8/1991 | Raines et al. | |
| 5,243,982 A | 9/1993 | Mostl et al. | |
| 5,298,020 A | 3/1994 | Stone | |
| 5,376,079 A * | 12/1994 | Holm | 604/191 |
| 5,411,490 A | 5/1995 | Tennican et al. | |
| 5,423,769 A | 6/1995 | Jonkman et al. | |
| 5,713,403 A | 2/1998 | Clusserath et al. | |
| 5,759,171 A | 6/1998 | Coelho et al. | |
| 5,975,367 A | 11/1999 | Coelho et al. | |
| 6,047,861 A * | 4/2000 | Vidal et al. | 222/137 |
| 6,077,447 A | 6/2000 | Coelho et al. | |
| 6,274,090 B1 | 8/2001 | Coelho et al. | |
| 6,355,024 B1 | 3/2002 | Small et al. | |
| 6,472,162 B1 * | 10/2002 | Coelho et al. | 435/13 |

* cited by examiner

*Primary Examiner*—Khoa D. Huynh
(74) *Attorney, Agent, or Firm*—Bernhard Kreten; Audrey A. Millemann; Weintraub Genshlea Chedia

(57) ABSTRACT

A loading station having a dispensing manifold for loading syringe pairs with thrombin and adhesive and clotting proteins for use as a biological adhesive. The resulting loaded syringe pairs are compatible with a variety of biological adhesive dispensers and may be used in a surgical setting.

8 Claims, 8 Drawing Sheets

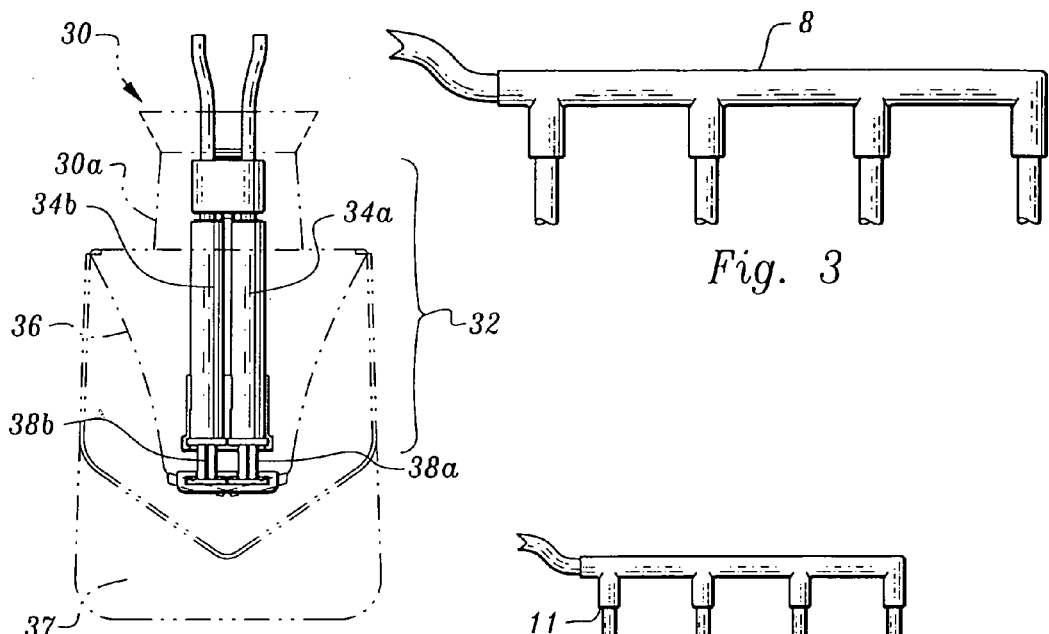
Fig. 3
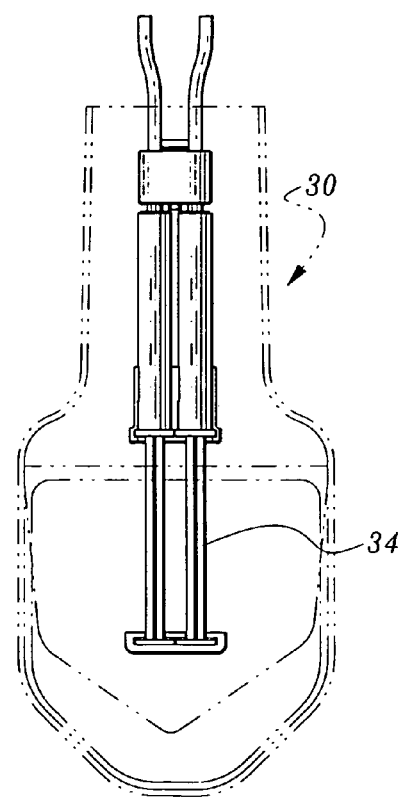
Fig. 4
Fig. 5
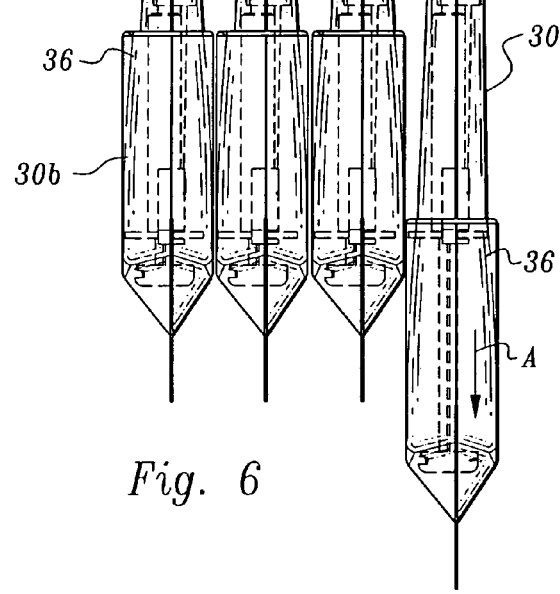
Fig. 6

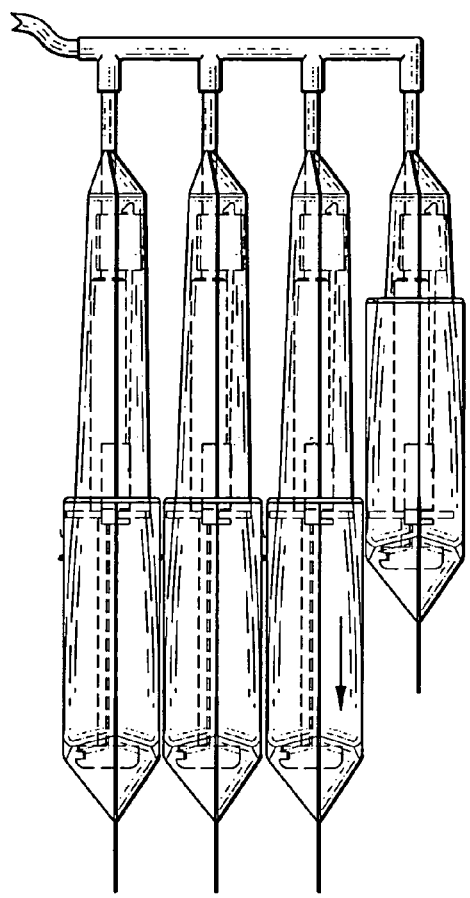
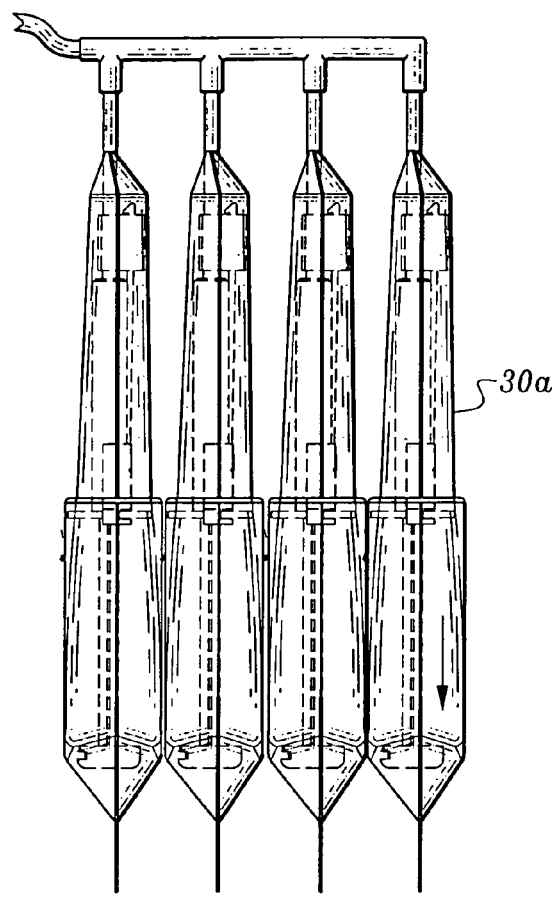
Fig. 10          Fig. 11
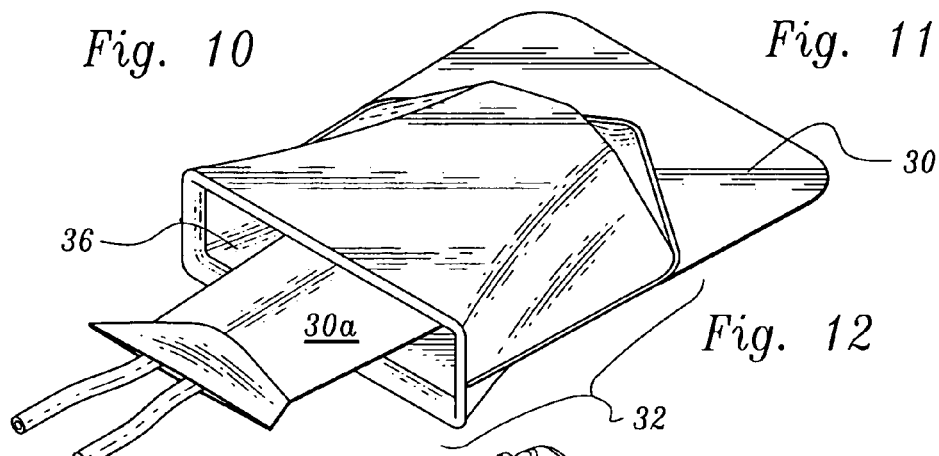
Fig. 12
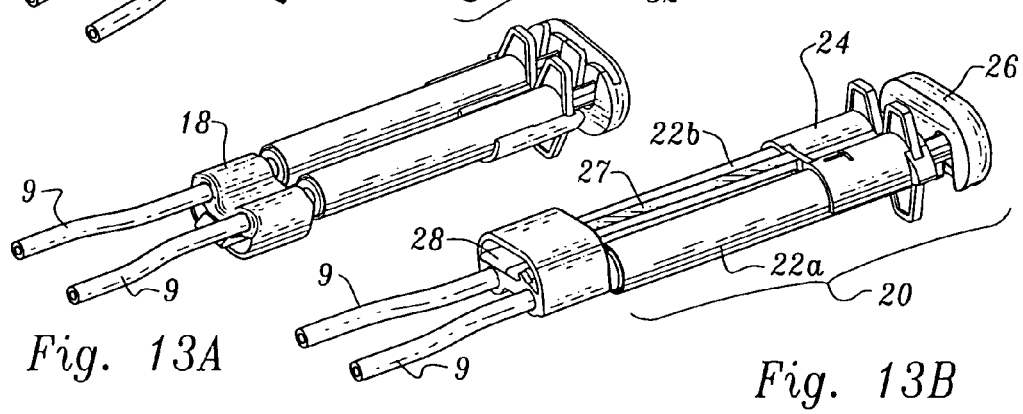
Fig. 13A          Fig. 13B

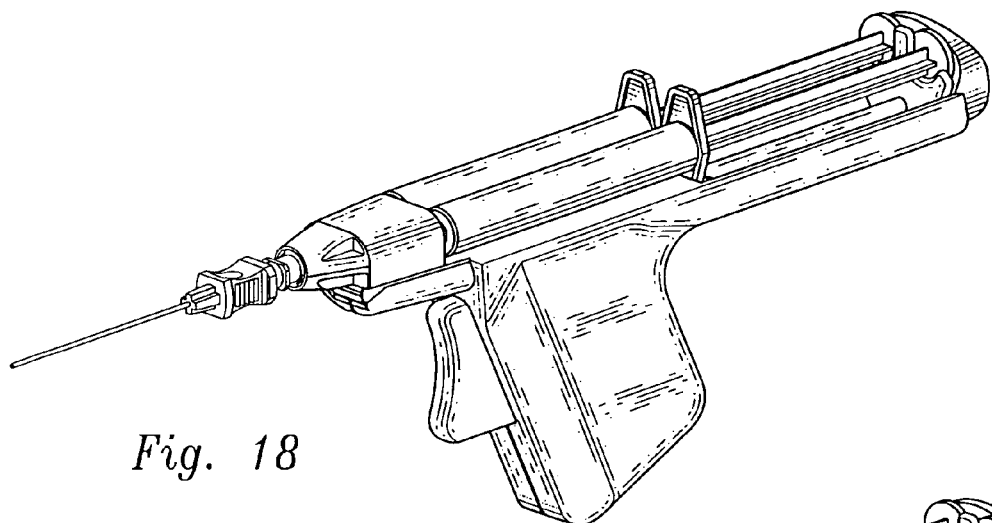
Fig. 18
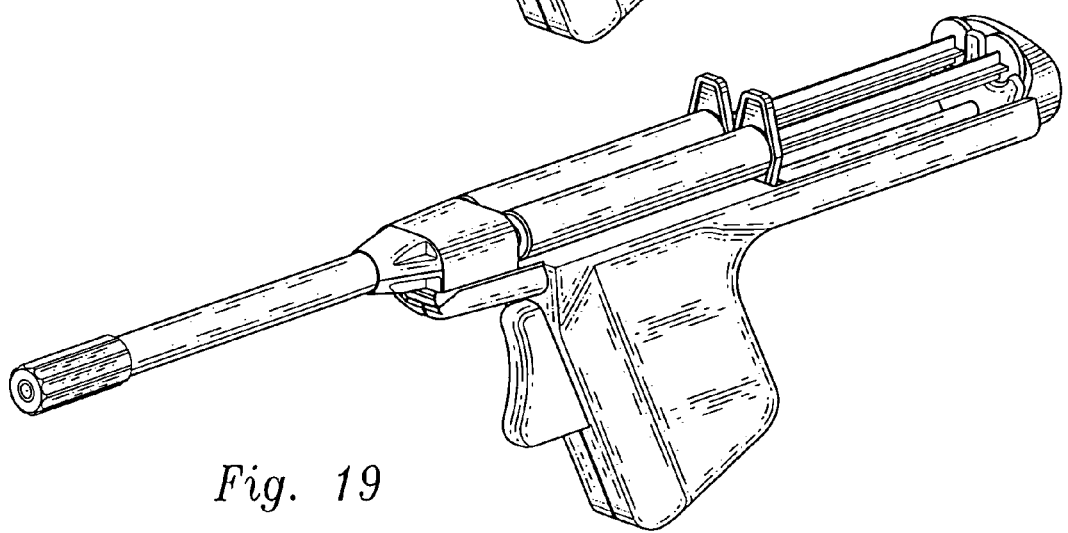
Fig. 19
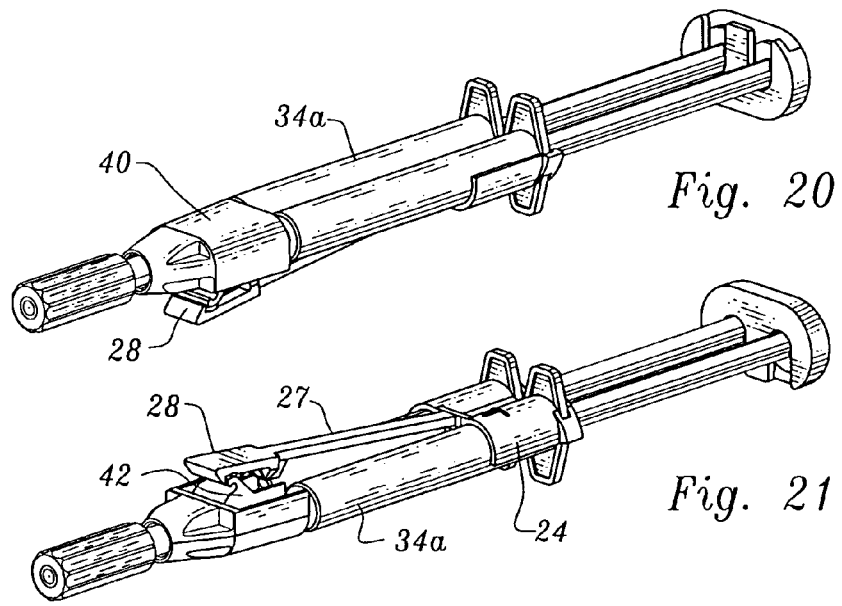
Fig. 20
Fig. 21

BIOLOGICAL ADHESIVE LOADING STATION AND METHOD

FIELD OF THE INVENTION

The following invention relates generally to instrumentalities and methodologies in preparing and administering biological adhesives. More specifically, the instant invention is directed to a method and apparatus for simultaneously loading dispensing assemblies with multiple components of biological glue and preparing the biological glue in a manner specific to the required need.

BACKGROUND OF THE INVENTION

This application represents applicant's ongoing efforts in the field of collecting, preparing, and dispensing components of biological adhesives.

U.S. Pat. No. 5,759,171 discloses a sprayer for fibrin glue configured with a pistol grip, barrel, and trigger, and adapted to hold two syringes containing the fibrin glue components. Activation of the trigger moves a plunger support, emptying the two syringes. Each syringe communicates with an outlet having an atomizer, and the atomizers are oriented to form the fibrin glue away from the tip of the sprayer, to prevent clogging.

U.S. Pat. No. 5,975,367 is directed to a hand-held dispenser for fibrin glue. The dispenser includes a spring-based rack that communicates with two syringes containing fibrin glue components such that the dispensed components may mix away from the tip of the dispenser. Drops or elongate lines of fibrin glue may be dispensed.

U.S. Pat. No. 6,077,447 reveals an apparatus, system and method for fractionating from whole blood, plasma, or other blood products the clotting factor known as fibrinogen, one component of a biological adhesive. A container is loaded with blood product containing fibrinogen, and the container is then put in registry with a heat transfer platen. The platen and container combination is rocked contemporaneously with temperature changes that induce a phase change in the blood product. The fibrinogen is then extracted from the container for subsequent use.

U.S. Pat. No. 6,274,090 B1 divulges an apparatus and method for preparing thrombin, another component of a biological adhesive. The thrombin component is extracted from donor plasma and converted to thrombin, while also removing contaminating proteins. Additionally, a system is described in which thrombin and adhesive and clotting proteins are simultaneously harvested from the same donor plasma, providing a more stable product than previously available. Both procedures occur in about one hour in a sterile environment, and are thereby optimized for use in a surgical setting.

WIPO application 00/74713A1 describes an improved thrombin processing unit that may be used with the methods revealed in U.S. Pat. No. 6,274,090 B1.

SUMMARY OF THE INVENTION

The present invention streamlines processing of thrombin and adhesive and clotting proteins to produce biological adhesives. Processing time is shorted, and the loading of syringes with the biological adhesives may be accomplished with improved sterility, less waste and more expeditious and particularly safer handling (e.g., from needle sticks) than heretofore experienced.

The present invention especially enhances the economics and practicalities of processing blood into biological adhesives. Customarily, a donor provides 500 mL (one "unit") of whole blood. This unit, when processed, yields 250–300 mL of plasma, which results in two components: 4.5–8.5 mL clotting proteins and about 8.5 mL of thrombin. Since the minimum quantum of biological adhesive needed comprises 1–2 mL, and because each component comprises approximately 50 percent of the two-part adhesive, one unit of whole blood can generate approximately 4 to 8 doses of biological adhesive. The instant invention loads and packages biological adhesive in convenient doses.

Syringe pair assemblies are attached to a dispensing manifold on a loading station. Processing units for each component of the biological adhesive are mounted near the dispensing manifold, with dispensing lines running therebetween. Blood product is introduced into the separate processing units for the components for the adhesive. The desired component is extracted from the blood product. The components run through separate dispensing lines into syringes such that each syringe pair contains one syringe loaded with each component. The syringe pairs are removed from the dispensing manifold and may be utilized in a variety of ways when in actual use. The syringes are compatible with an adhesive spraying apparatus, such as the spraying means as recited in claims 3, 4, 7, and 8, and may also be used with a heating station to maintain the adhesive components at an optimal temperature for use in a surgical setting.

OBJECTS OF THE INVENTION

Accordingly, it is a primary object of the present invention to provide a new and novel device and method for loading multiple syringes with biological glue components.

It is a further object of the present invention to provide a device and method as characterized above in which the loading procedure is independent of the application for which the biological glue is utilized.

It is a further object of the present invention to provide a device and method as characterized above which minimizes waste in loading the biological glue dispenser, improves efficiency and maintains sterility.

It is a further object of the present invention to provide a device and method as characterized above that minimizes clogging of the dispenser in delivering the biological glue to the intended site.

It is a further object of the present invention to provide a device and method as characterized above that may be utilized in a surgical setting.

Viewed from a first vantage point, it is an object of the present invention to provide an apparatus for collecting thrombin and clotting proteins, comprising, in combination: a first conduit operatively connected to a source of thrombin; and a second conduit operatively connected to a source of clotting proteins, each said conduit operatively connected to a plurality of dispensing means.

Viewed from a second vantage point, it is an object of the present invention to provide a method for loading dispensing means with thrombin and clotting proteins, the steps including: attaching a plurality of said dispensing means to separate dispensing lines containing thrombin and clotting proteins; manipulating said plurality of dispensing means to purge air in each of said dispensing lines; and sequentially filling said plurality of dispensing means through each of said dispensing lines.

BRIEF DESCRIPTION OF THE DRAWINGS

FIG. 3 is a view of the dispensing manifold.

FIG. 4 is a view of the syringe pair assembly in its membrane in the contracted position.

FIG. 5 is a view of the syringe pair assembly in its membrane in the extended position.

FIG. 6 depicts the first step in a loading process, extending the syringe pair assembly in the endmost position.

FIG. 10 depicts the fifth step in a loading process, filling the syringe pair assembly third from the support.

FIG. 11 depicts the sixth step in a loading process, filling the syringe pair assembly fourth from the support.

FIG. 12 is a view of the syringe pair assembly in its contracted position within its associated membrane.

FIG. 13A is a top view of a syringe pair assembly that may be used with the loading station of the present invention.

FIG. 13B is a bottom view of a syringe pair assembly that may be used with the loading station of the present invention.

FIG. 18 depicts the spraying apparatus and a syringe pair assembly having a third attachment.

FIG. 19 depicts the spraying apparatus and a syringe pair assembly having a fourth attachment.

FIG. 20 is a top view of a syringe pair assembly having an output coupling and spray nozzle.

FIG. 21 is a bottom view of the syringe pair assembly having an output coupling and spray nozzle.

DESCRIPTION OF PREFERRED EMBODIMENTS

Figure 1:
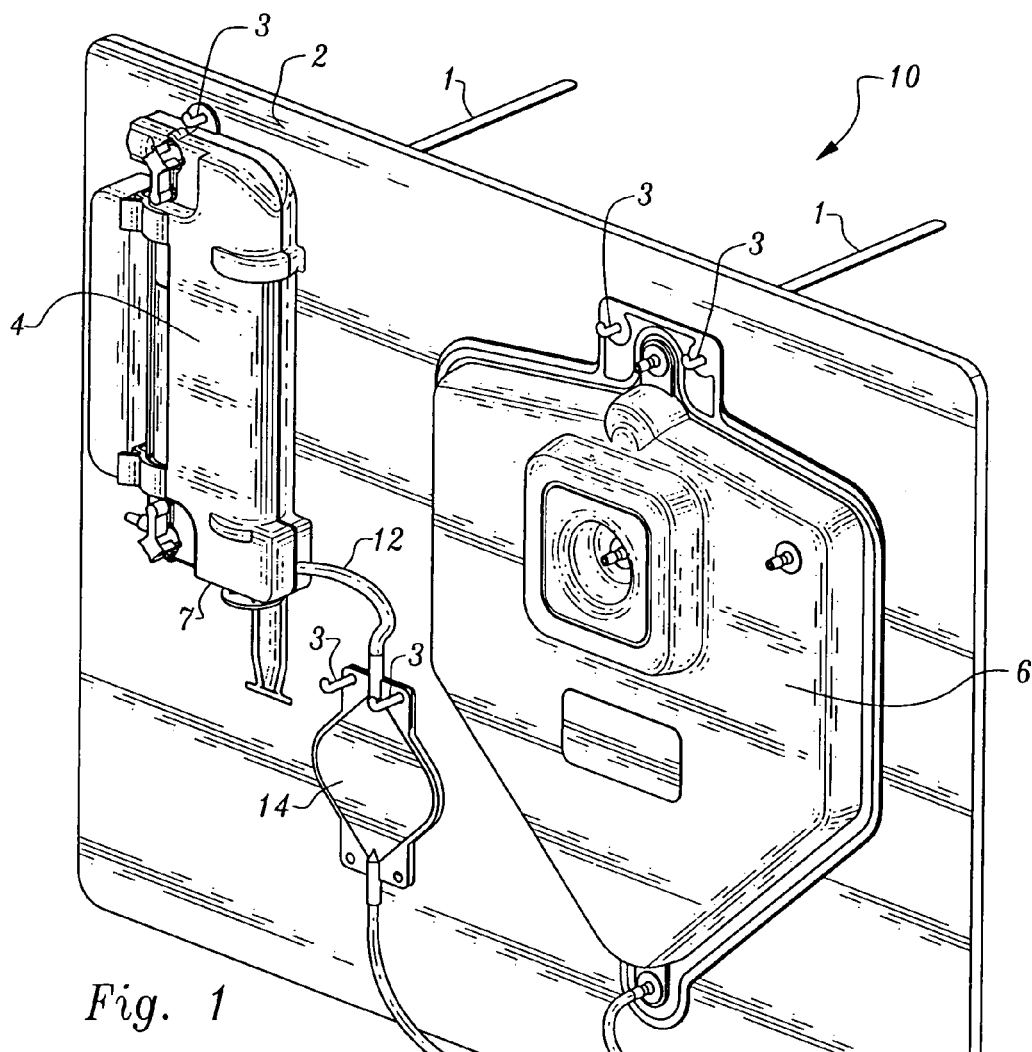
FIG. 1 is a perspective view of the loading station.

Considering the drawings, wherein like reference numerals denote like parts throughout the various drawing figures, reference numeral 10 as shown in FIG. 1 is directed to the loading station according to the present invention.

Figure 2:
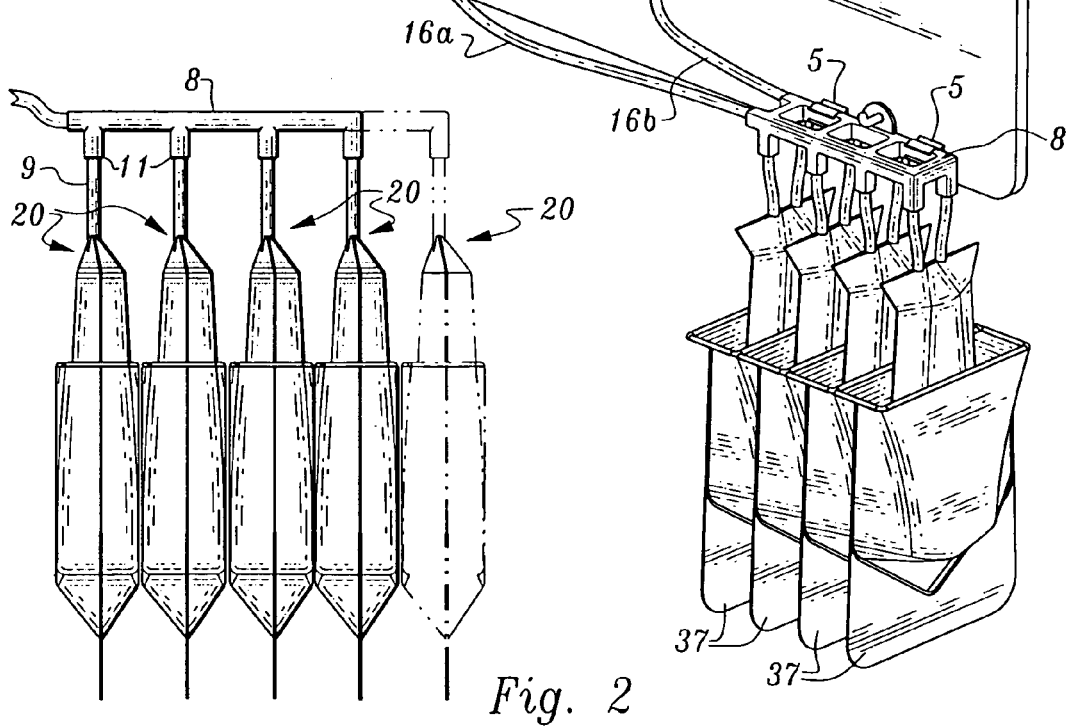
FIG. 2 is a side view of the dispensing manifold with attached syringes within their associated membranes.
Figure 9:
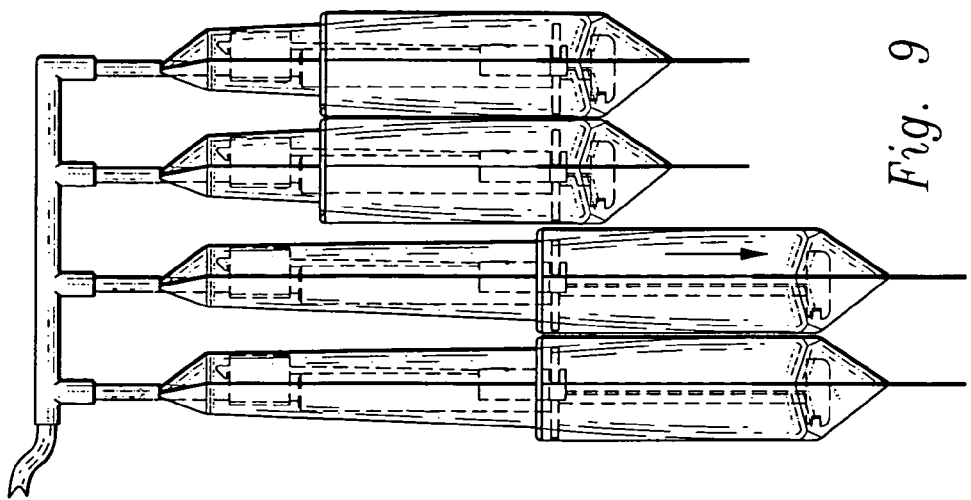
FIG. 9 depicts the fourth step in a loading process, filling the syringe pair assembly second from the support.
Figure 8:
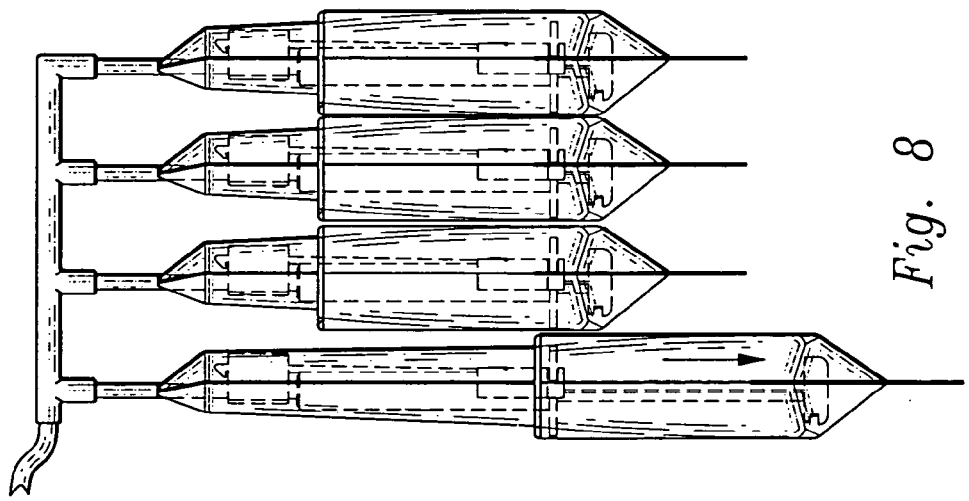
FIG. 8 depicts the third step in a loading process, filling the syringe pair assembly closest to the support.
Figure 7:
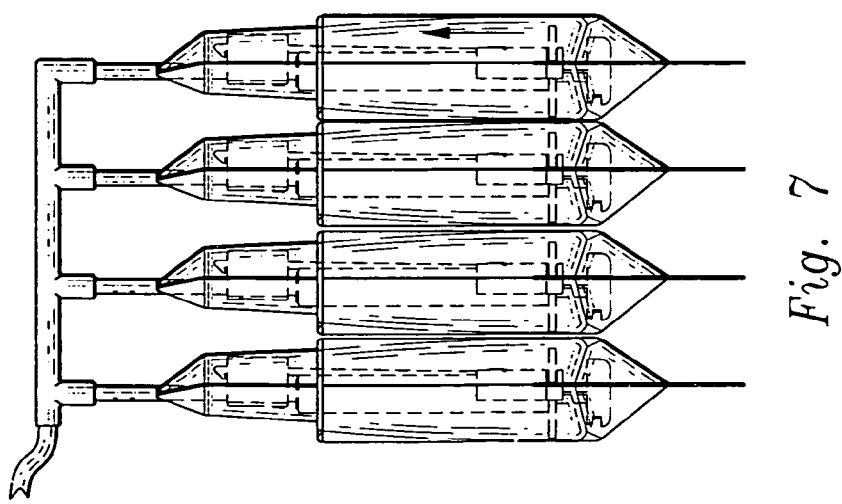
FIG. 7 depicts the second step in a loading process, contracting the syringe pair assembly in the endmost position.

In its essence, the loading station 10 includes a support 2, to which the following are mounted: a thrombin processing unit 4, a clotting and adhesive proteins processing unit 6, and a dispensing manifold 8. Each unit 4, 6 has a separate dispensing line 16a, 16b to the dispensing manifold 8 as shown in FIG. 1, to maintain sequestration of each component of the biological glue. The outlet 12 connected to the thrombin processing unit 4 leads into a reserve vessel 14, whereby pressure from a thrombin syringe 7 causes thrombin to enter the reserve vessel 14. Rods 1 suspend support 2. Hooks 3 support the thrombin processing unit 4, the clotting and adhesive proteins processing unit 6, and reserve vessel 14. Clips 5 support the dispensing manifold 8. The dispensing manifold 8 is preferably oriented to load a plurality of syringe pair assemblies 20 (FIG. 13B) with components of the biological glue. FIG. 2 depicts four such syringe pair assemblies 20, but it is also observed from FIG. 2 that additional assemblies 20 may be present.

Figures 14, 15:
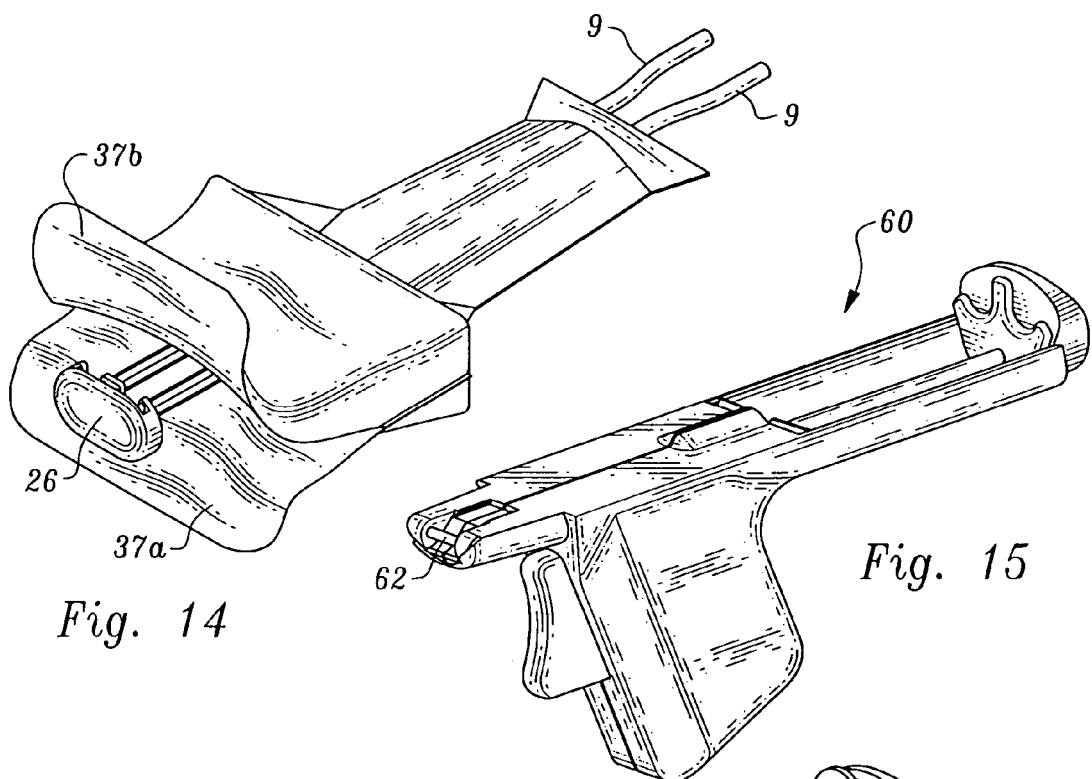
FIG. 14 is a view of the syringe pair assembly in its extended position within its associated membrane.
FIG. 15 depicts a spraying apparatus for use with the syringe pair assembly of the present invention.
Figure 16:
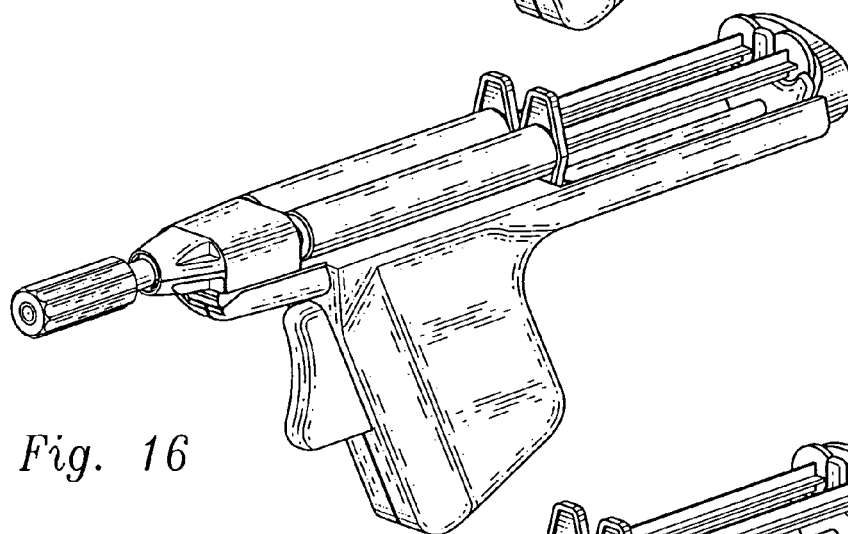
FIG. 16 depicts the spraying apparatus and a syringe pair assembly having a first attachment.
Figure 17:
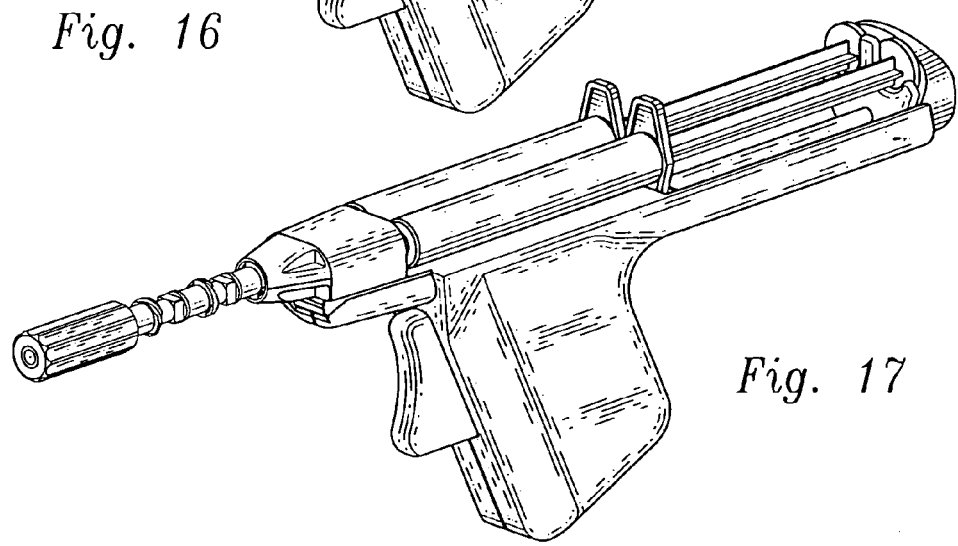
FIG. 17 depicts the spraying apparatus and a syringe pair assembly having a second attachment.

The syringe pair assembly 20 is pictured in FIGS. 13A, 13B. The assembly 20 includes two syringes (dispensing means) 22a, 22b; a barrel-holding frame 24; and a plunger connector 26. A fitting 18 is also present, the fitting 18 adapted to frictionally hold the syringe pair assembly 20 together and link to the dispensing manifold 8 via tubing 9. The barrel-holding frame 24 includes a spring-based plastic retaining member 28; in FIG. 13B, the retaining member 28 secures the barrel-holding frame 24 to the fitting 18. The spring 27 is shown as a resilient leaf (FIG. 13B) integral with frame 24 and leading to the retainer 28. The assembly 20 is housed inside a membrane 30, particularly during loading. The membrane 30 is preferably flexible plastic, formed with a gathered (doubled-over) portion 32 about the assembly 20. The gathered portion 32 is formed by creating pleats 36 using "accordion"-type folds in the membrane 30, with a first layer 30a (FIG. 11) of the membrane 30 proximate the syringe pair assembly 20 (FIGS. 4, 12) and an outer layer 30b which moves from an overlying position (relative to the first layer 30a) to a coextensive position after loading a syringe pair assembly 20, one with clotting proteins and the other with thrombin. One end of the membrane 30 is sealed over the tubing 9 that connects to the dispensing line 16a, 16b via dispensing manifold 8. The other end of the membrane 30 is also closed and is deployed about the syringe plungers 38a, 38b, to allow an operator to grasp and extend the plunger end during filling of the syringe pair assembly 20 without exposure to ambient conditions. Downward force, shown by the arrow A in FIG. 6, while grasping the plunger end and the membrane 30 allows the pleats 36 of the gathered portion 32 to expand while always encasing the now-fully extended assembly 20 (FIGS. 5, 14). The plunger end of the membrane 30 will be opened (FIG. 14) in an operatory to allow access to the filled syringe pair assembly 20 during a surgical procedure. As shown in FIG. 14, a free end 37 of the membrane 30 shows the membrane as formed from the parts 37a, 37b, sealed together but separable (by peeling apart) to expose plunger connector 26 of the loaded syringe pair. Thus, the loaded syringe pair is maintained sterile until actual use in surgery.

The procedure for loading the assemblies 20 with thrombin and adhesive and clotting proteins is shown in FIGS. 6–11. Before loading, all assemblies 20 are encased in membranes 30 and attached to the dispensing manifold 8 using the fittings 18. The assembly 20 located furthest from the end of the dispensing manifold 8 is preferably drawing on the dispensing lines 16a, 16b by extending the syringe plungers (FIG. 6) to fill the dispensing lines 16a, 16b and dispensing manifold 8. It is then preferably returned to its original contracted position (FIG. 7) after having expelled excess air. Beginning from the opposite end, each assembly 20 is successively extended to fill the syringe barrels 34a, 34b with the appropriate amounts of thrombin and clotting and adhesive proteins (FIGS. 8–11). After all assemblies 20 are loaded, each assembly 20 and its associated membrane 30 may then be removed from the dispensing manifold 8 by heat sealing or crimping tubing 9 and severing at the crimp or heat seal, or upstream at the juncture 11 of the tubing 9 with the manifold 8.

To remove assembly 20 from membrane 30, spring 27 is depressed toward syringes 22a, 22b to release retaining member 28 from mating catch on fitting 18. Syringes 22a, 22b are twisted and pulled away from fitting 18, allowing assembly 20 to reside loose within membrane 30. Membrane 30 is then peeled apart, as described earlier, to remove assembly 20.

Figure 22A:
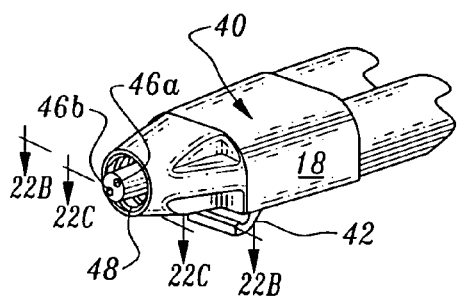
FIG. 22A is a perspective view of the output coupling.
Figure 22B:
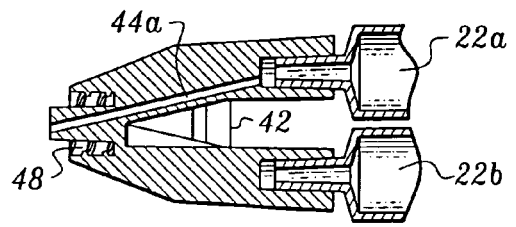
FIG. 22B is a view along the section 22B—22B, depicting the outlet path of the contents of one syringe of the syringe pair assembly.
Figure 22C:
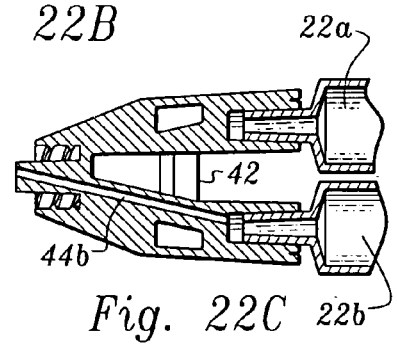
FIG. 22C is a view along the section 22C—22C, depicting the outlet path of the contents of the other syringe of the syringe pair assembly.
Figure 23:
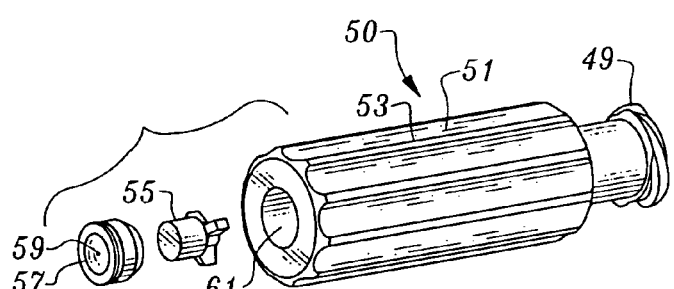
FIG. 23 is an exploded view of a nozzle attachment that may be associated with the output coupling of the present invention.
Figure 24:
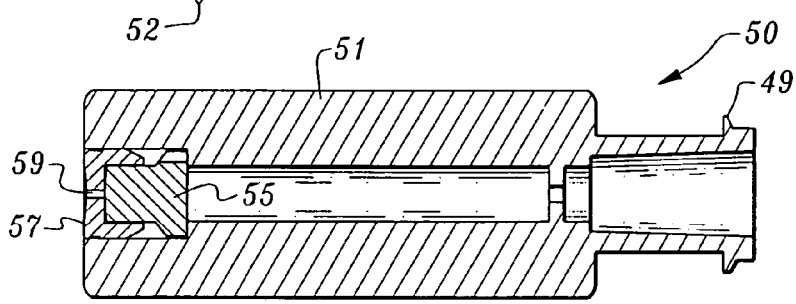
FIG. 24 is a cutaway view of a nozzle attachment that may be associated with the output coupling of the present invention.
Figure 25:
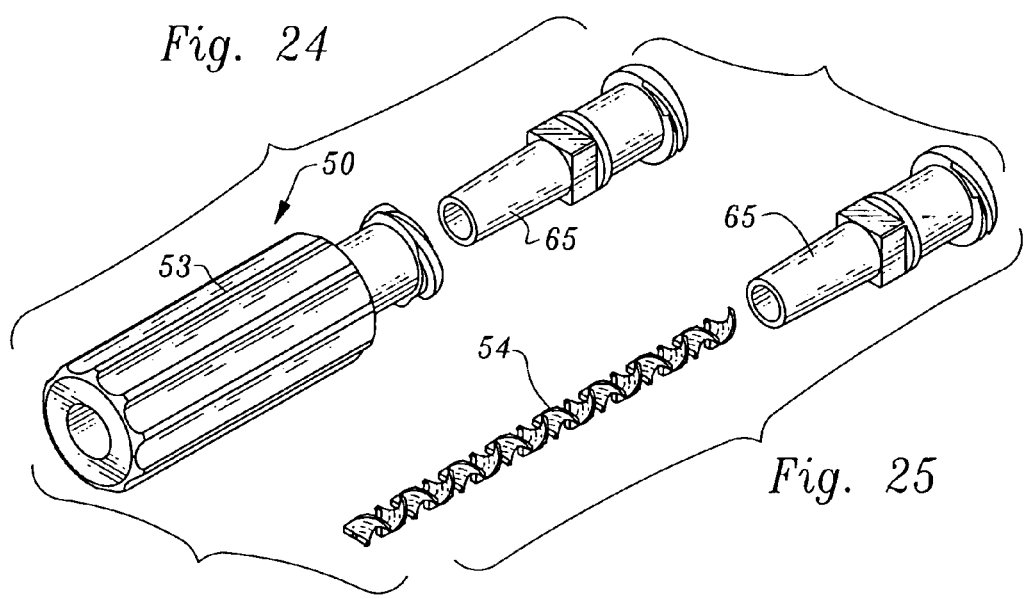
FIG. 25 is an exploded view of attachments that may be associated with the output coupling of the present invention, one having a spray nozzle and the other having a helical mixing path.
Figure 26:
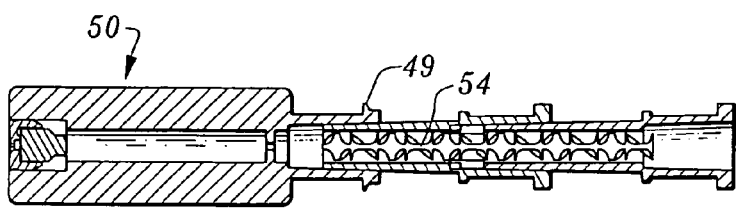
FIGS. 26 and 27 are cutaway views of lengthening attachments having helical mixing paths and spray nozzle ends that may be associated with the present invention.
Figure 27:
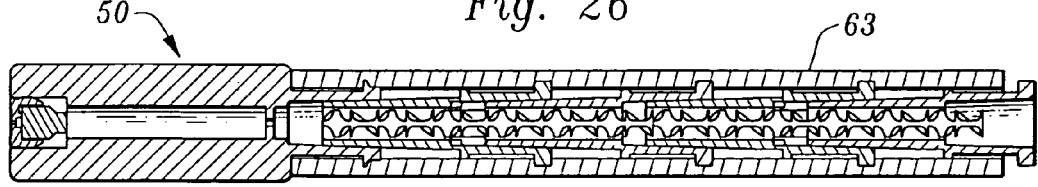

Once filled and removed, the assembly 20 may be fitted with an outlet coupling 40, shown in FIG. 22A. The retaining member 28 latches to a catch 42 on coupling 40 (FIG. 21). As shown in FIGS. 22B and 22C, the outlet coupling 40 equips each syringe 22a, 22b with a separate exit path 44a, 44b, such that the thrombin and the adhesive and clotting proteins may exit separately as lines or dots from ports 46a, 46b in the outlet coupling 40, thereby preventing clogging of the outlet coupling 40. A recessed threaded area 48 is located proximate the ports 46a, 46b of the outlet coupling 40 to support a dispensing attachment.

The recessed female threaded area 48 of the outlet coupling 40 may receive any of a variety of dispensing attachments having a threaded end 49; examples of attachments are shown in FIGS. 16–21, 23–27. The spray nozzle 50 shown in FIGS. 23, 24 may be combined with lengthening attachments, shown in FIGS. 25–27. These lengthening attachments are preferably constructed with an external cylindrical shroud 63 which overlies intermediate sleeves 65 that support a central internal helical path 54 to enhance admixture of the thrombin and the adhesive clotting proteins. Mixing of the thrombin with the adhesive and clotting proteins occurs within the chosen attachment and is dispensed out the spray end 52 of the spray nozzle 50 for precise placement. The spray nozzle 50 is comprised of a barrel 51 having tactile enhancing, longitudinally extending peripheral ribs 53. The end 52 includes a flow diverter 55 and a restrictor orifice body 57 having an orifice 59. The body 57 is press-fit into bore 61 of nozzle 50 or attached by other means.

FIG. 15 depicts a dispensing apparatus 60 adapted to receive the syringe pair assembly 20. In this embodiment, the outlet coupling 40 connects to the dispensing apparatus 60 by registering a clasp 42 present on the underside of the outlet coupling 40 with a pivot 62 (FIG. 15). The syringe pair assembly 20 is inserted into the outlet coupling 40 and the frame 24 is removed.

Figure 28:
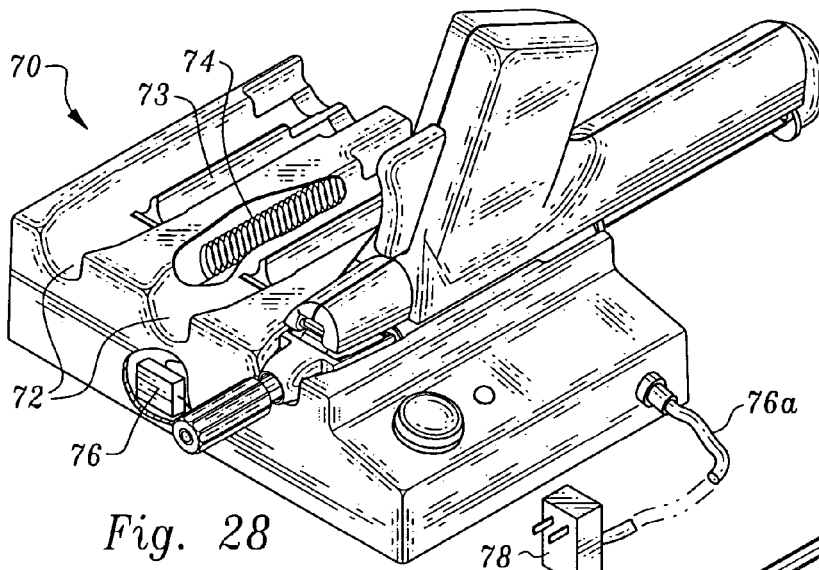
FIG. 28 depicts a heating apparatus that receives the syringe pair assembly of the present invention, here used with the spraying apparatus of FIG. 15.
Figure 29:
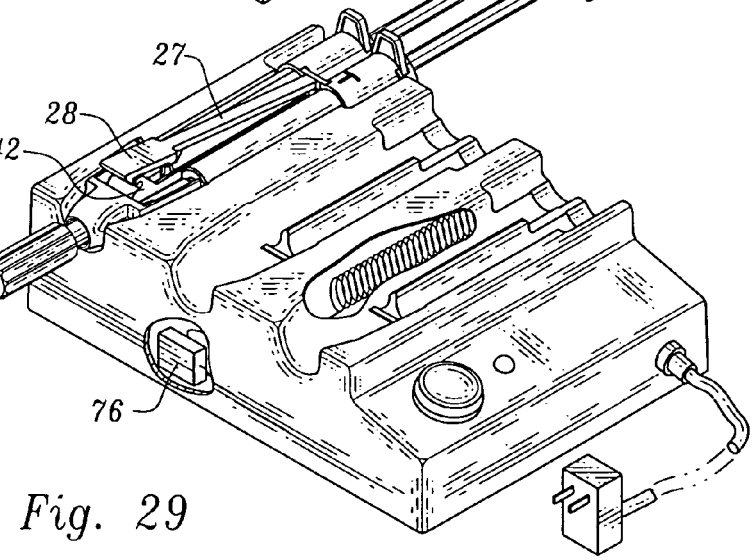
FIG. 29 depicts a heating apparatus that receives the syringe pair assembly of the present invention, here used with the assembly shown in FIGS. 20 and 21.

FIGS. 28, 29 depict a heating apparatus 70, which includes a plurality of elongated arctuate indentations 72, each shaped with projecting saddles 73 to receive a syringe pair assembly 20 and to ensconce a large portion of each syringe's barrel. The heating apparatus 70 contains resistive heating elements 74 to maintain the assemblies 20 at a constant temperature for heat transfer through indentations 72 and saddles 73. The power cord 76 is connected to a power supply 78, which in turn plugs into an electrical supply outlet. A sensor and microcontroller 76 optimize temperature. Compatible dispensing assemblies include, but are not limited to, the spraying apparatus 60 of FIG. 15 and the basic syringe setup depicted in FIGS. 20, 21. Thus, the prepared biological glue is readily available for use during the medical procedure.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A method for loading dispensing means with thrombin and clotting proteins, the steps including:

attaching a plurality of said dispensing means to separate dispensing lines containing thrombin and clotting proteins;

manipulating said plurality of dispensing means to purge air in each of said dispensing lines;

sequentially filling said plurality of dispensing means through each of said dispensing lines;

clustering said plurality of dispensing means in pairs, with one of each said pair of dispensing means receiving thrombin and the other receiving clotting proteins;

equipping each said dispensing means with a removable fitting for connection to one said dispensing line;

securing each said pair of dispensing means in a frame, said frame including a retaining member; and ensconcing each of said pairs of dispensing means in a membrane.

2. The method of claim 1 further including the step of:

maintaining contents of said dispensing means at a desired temperature after filling.

3. The method of claim 1 further including the step of:

introducing each said pair of dispensing means into a spraying means, said spraying means having means for simultaneous delivery of the thrombin and clotting proteins.

4. The method of claim 3 further including the step of:

maintaining contents of said dispensing means in said spraying means at a desired temperature after filling.

5. A method for loading dispensing means with thrombin and clotting proteins, the steps including;

attaching a plurality of said dispensing means to separate dispensing lines containing thrombin and clotting proteins;

manipulating said plurality of dispensing means to purge air in each of said dispensing lines;

sequentially filling said plurality of dispensing means through each of said dispensing lines;

clustering said plurality of dispensing means in pairs, with one of each said pair of dispensing means receiving thrombin and the other receiving clotting proteins;

equipping each said dispensing means with a removable fitting for connection to one said dispensing line;

securing each said pair of dispensing means in a frame, said frame including a retaining member;

forming a membrane, said membrane having a gathered portion of accordion folds; and ensconcing each said pair of dispensing means in a separate membrane such that said membrane opens at an end opposite said dispensing lines, whereby removal or adjustment of said dispensing means may occur.

6. The method of claim 5 further including the step of:
maintaining contents of said dispensing means at a desired temperature after filling.

7. The method of claim 5 further including the step of:
introducing each said pair of dispensing means into a spraying means, said spraying means having means for simultaneous delivery of the thrombin and clotting proteins.

8. The method of claim 7 further including the step of:
maintaining contents of said dispensing means in said spraying means at a desired temperature after filling.

* * * * *